United States Patent
Loehl et al.

(10) Patent No.: US 6,482,418 B1
(45) Date of Patent: Nov. 19, 2002

(54) COSMETIC AND/OR PHARMACEUTICAL PREPARATIONS COMPRISING DIALKENYL CARBONATES

(75) Inventors: Thorsten Loehl, Duesseldorf (DE); Thomas Gassenmeier, Dusseldorf (DE); Joerg Kahre, Leichlingen (DE); Hermann Hensen, Haan (DE); Holger Tesmann, Juechan (DE); Achim Ansmann, Erkrath (DE)

(73) Assignee: Henkel Kommanditgesellschaft auf Aktien, Duesseldorf (DE)

(*) Notice: Subject to any disclaimer, the term of this patent is extended or adjusted under 35 U.S.C. 154(b) by 0 days.

(21) Appl. No.: 09/202,378
(22) PCT Filed: Jun. 3, 1997
(86) PCT No.: PCT/EP97/02867
§ 371 (c)(1), (2), (4) Date: Jun. 21, 1999
(87) PCT Pub. No.: WO97/47282
PCT Pub. Date: Dec. 18, 1997

(30) Foreign Application Priority Data

Jun. 12, 1996 (DE) .......... 196 23 383
Mar. 12, 1997 (DE) .......... 197 10 154

(51) Int. Cl.[7] .............................. A61K 6/00
(52) U.S. Cl. ............... 424/401; 514/937; 514/938; 510/417; 252/56
(58) Field of Search ............ 424/401; 514/937, 514/938; 252/56; 510/417

(56) References Cited

U.S. PATENT DOCUMENTS

| | | | |
|---|---|---|---|
| 4,172,887 A | 10/1979 | Vanlerberghe et al. | 424/70 |
| 4,395,370 A | 7/1983 | Boden et al. | 260/463 |
| 5,387,374 A | 2/1995 | Westfechtel et al. | 252/56 S |
| 5,545,731 A * | 8/1996 | Weuthen | 424/70.1 |
| 5,795,978 A * | 8/1998 | Ansmann et al. | 536/120 |

FOREIGN PATENT DOCUMENTS

| | | |
|---|---|---|
| DE | 11 65 574 | 3/1964 |
| DE | 20 24 051 | 5/1986 |
| DE | 40 40 154 | 6/1992 |
| DE | 41 19 890 | 12/1992 |
| DE | 4119890 * | 12/1992 |
| DE | 4404200 * | 12/1992 |
| DE | 42 09 338 | 9/1993 |
| DE | 43 17 683 | 12/1994 |
| DE | 44 04 200 | 8/1995 |
| DE | 4404200 A1 * | 8/1995 |
| FR | 2252840 | 10/1973 |
| GB | 962 919 | 8/1961 |

OTHER PUBLICATIONS

Kosmetik Und Aerosole, "Seifen–Fette–Oele–Wachse" 100 (1974) pp. 173–177.
Chemical Review 96, (1996) pp. 951–976.
"Kosmetische Faerbemittel" der Farbstoffkommission der Deutschen Forschungsgemeinschaft, Verlag Chemie, Weinheim, (1984) pp. 81–106.
Derwent Patent Abstract (WPAT) No. 96–006868/01, Apr. 1994.
Derwent Patent Abstract (WPAT) No. 93–000537/01, Dec. 1993.
Derwent Patent Abstract (WPAT) No. 92–209099/26, Jun. 1992.
Derwent Patent Abstract (WPAT) No. 95–007522/02, Dec. 1994.
Derwent Patent Abstract (WPAT) No. 66–0158F/00, Aug. 1960.
Derwent Patent Abstract (WPAT) No. 71–736115/46, Oct. 1979.
Derwent Patent Abstract (WPAT) No. 75–39724W/24, Jun. 1975.
Derwent Patent Abstract (WPAT) No. 95–284119/38, Aug. 1975.
Derwent Patent Abstract (WPAT) No. 93–320722/40, Sep. 1993.

* cited by examiner

Primary Examiner—Thurman K. Page
Assistant Examiner—Lakshmi Channavajjala
(74) Attorney, Agent, or Firm—John E. Drach; Aaron R. Ettelman

(57) ABSTRACT

The invention relates to new cosmetic and/or pharmaceutical formulations containing
(a) dialkyl carbonates corresponding to formula (I):

$$R^1O(CH_2CH_2O)_n\overset{\overset{\displaystyle O}{\|}}{C}(OCH_2CH_2)_{\overline{m}}OR^2 \qquad (I)$$

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another stand for 0 or numbers of 1 to 100, and
(b) emulsifiers.

The formulations are distinguished by particular sensorial properties, the dialkyl carbonates proving to be as effective as the silicone oils which they are intended to replace.

20 Claims, No Drawings

COSMETIC AND/OR PHARMACEUTICAL PREPARATIONS COMPRISING DIALKENYL CARBONATES

BACKGROUND OF THE INVENTION

1. Field of the Invention

This invention relates to cosmetic and/or pharmaceutical formulations which contain selected dialkyl carbonates as oils and, in addition, emulsifiers, preferably alkyl oligoglucosides, and to the use of the dialkyl carbonates as substitutes for silicone oils.

2. Discussion of the Related Art

Silicones are used in skin and hair cosmetics as additives for influencing feel and shine. Unfortunately, a disadvantage of silicones in this regard is the so-called build-up effect. The build-up effect occurs when silicone-containing products are repeatedly applied to skin or hair where they build up a layer of polymers which is difficult to remove simply by washing. In the case of hair in particular, other treatments, for example waving or coloring, can be affected and possibly impaired by the build-up effect. Another disadvantage of many silicone types is their poor biological degradability. The use of silicones in cosmetics has been reviewed, for example, by K. Schnurrbusch in Seifen-Fette-Öle-Wasche 100, 173 (1974).

The use of Guerbet carbonates based on alcohols containing at least 6 carbon atoms as oils for cosmetic formulations is known from DE-A1 40 40 154 (Henkel). DE-A1 43 17 683 (Henkel) relates to carbonates based on ethoxylated fatty alcohols and to their use for cleaning hard surfaces.

Accordingly, the problem addressed by the present invention was to find substitutes for silicones which would not accumulate in use, but which would nevertheless show comparable performance properties in regard to feel and shine.

DESCRIPTION OF THE INVENTION

The present invention relates to cosmetic and/or pharmaceutical formulations containing:

(a) dialkyl carbonates corresponding to formula (I);

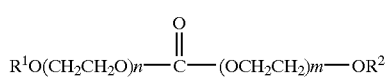

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another stand for 0 or numbers of 1 to 100, and (b) emulsifiers.

It has surprisingly been found that, in sensorial terms, formulations containing the selected dialkyl carbonates perform at least as well as silicone oils in regard to feel and shine without undesirably accumulating on the skin and hair. The present invention also includes the observation that the dialkyl carbonates corresponding to formula (I) are capable of covering a broad spectrum of different sensorial properties.

Dialkyl Carbonates

Dialkyl carbonates are basically known compounds even through some of the claimed compounds are being described for the first time in the present specification. Basically, they may be prepared by transesterification of dimethyl or diethyl carbonate with the hydroxy compounds mentioned using known methods. A review of these methods can be found, for example, in Chem. Rev. 96, 951 (1996). Dialkyl carbonates corresponding to formula (I) which are particularly suitable for solving the stated problem satisfy one of the following requirements:

(a) $R^1$ is a linear alkyl group containing 8 to 18 carbon atoms or a 2-ethylhexyl group and $R^2$ has the same meaning as $R^1$ or represents methyl;

(b) $R^1$ is a linear alkyl group containing 12 to 18 carbon atoms, $R^2$ has the same meaning as $R^1$ or represents methyl and n and m stand for numbers of 1 to 10;

(c) $R^1$ is a residue of a polyol selected from the group consisting of glycerol, alkylene glycols, technical oligoglycerol mixtures, methylol compounds, lower alkyl glucosides, sugar alcohols, sugars and aminosugars and $R^2$ has the same meaning as $R^1$ or represents a linear or branched alkyl group containing 8 to 12 carbon atoms or methyl.

Typical examples of dialkyl carbonates belonging to the two groups (a) and (b) are complete or partial transesterification products of dimethyl and/or diethyl carbonate with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof formed, for example, in the high-pressure hydrogenation of technical methyl esters based on fats and oils or aldehydes from Roelen's oxosynthesis and as monomer fraction in the dimerization of unsaturated fatty alcohols. The transesterification products of the lower carbonates with the alcohols mentioned in the form of their adducts with 1 to 100, preferably 2 to 50 and more preferably 5 to 20 moles of ethylene oxide are also suitable.

The carbonates of group (c) are being described for the first time in the present specification. They are compounds which are obtained by complete or partial transesterification of dimethyl and/or diethyl carbonate with polyols. Polyols suitable for the purposes of the invention preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and also polyethylene glycols with an average molecular weight of 100 to 1,000 dalton;

technical oligoglycerol mixtures with a degree of self-condensation of 1.5 to 10, for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, more particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

This reaction can of course not only result in replacement of a methyl or ethyl group by a polyol residue, it also gives a mixture in which several hydroxy groups or even all the hydroxyl groups of the polyol are attached to carbonate groups so that an oligomeric or polymeric net structure may even be obtained. In the context of the invention, compounds of this type are also meant to fall within the scope of general formula (I).

Emulsifiers

Suitable emulsifiers are, for example, nonionic surfactants from at least one of the following groups:

(1) products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group;

(2) $C_{12/18}$ fatty acid monoesters and diesters of products of the addition of 1 to 30 moles of ethylene oxide to glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate or polyglycerol poly-12-hydroxystearate. Mixtures of compounds from several of these classes are also suitable;

(7) products of the addition of 2 to 15 moles of ethylene oxide to castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) trialkyl phosphates and mono-, di- and/or tri-PEG-alkyl phosphates;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol;

(13) polyalkylene glycols and

(14) hydrophobicized polyacrylates, for example of the Pemulen type.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Alkyl and alkenyl oligoglycosides are known nonionic surfactants which correspond to formula (II):

where $R^3$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry, for example by acid-catalyzed acetalization of glucose with fatty alcohols. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an, analytically determined calculated quantity which is generally a non-whole number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^3$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^3$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Other suitable emulsifiers are zwitterionic surfactants of the betaine type. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methyl-quaternized difatty acid triethanolamine ester salts, being particularly preferred. All in all, it is preferred to use alkyl oligoglucosides, betaines and polyglycerol poly-12-hydroxystearates. The formulations normally contain the dialkyl carbonates and the emulsifiers in quantities of 0.1 to 20% by weight and preferably in quantities of 1 to 10% by weight, based on the formulations, the ratio by weight of the dialkyl carbonates to the emulsifiers generally being from 30:1 to 1:20 and preferably from 5:1 to 1:10. This ratio is preferably from 1:5 to 1:10 in the case of rinse-off products and from 5:1 to 1:1 in the case of leave-on products.

Commercial Applications

The dialkyl carbonates to be used in accordance with the present invention have excellent sensorial properties on the skin and hair which are in no way inferior to those of silicone oils. Accordingly, the present invention also relates to their use as substitutes for silicone oils for the production of cosmetic and/or pharmaceutical formulations.

Cosmetic and/or Pharmaceutical Formulations

The formulations according to the invention, for example hair shampoos, hair lotions, foam baths, cremes, lotions or emollients, may additionally contain mild surfactants, other oils, superfatting agents, stabilizers, waxes, consistency regulators, thickeners, cationic polymers, biogenic agents, antidandruff agents, film formers, preservatives, hydrotropes, solubilizers, UV filters, insect repellents, self-tanning agents, dyes and fragrances as further auxiliaries and additives.

Typical examples of suitable mild surfactants, i.e. surfactants with particular dermatological compatibility, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, preferably based on wheat proteins.

Suitable other oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, dialkyl ethers, silicone oils and/or aliphatic or naphthenic hydrocarbons.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency regulators are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®L Grunau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyamino-polyamides as described, for example, in FR-A 225840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol AZ-1 of Miranol.

Since the problem addressed by the present invention was inter alia to replace silicone compounds in the formulations, the additional presence of these compounds, although not essential, is not ruled out in principle. Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable antidandruff agents are climbazol, octopirox and zinc pyrethion. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4-methoxybenzophenone), dibenzoyl methanes, salicylate esters, 2-phenyl benzimidazole-5-sulfonic acid, 1-(4-tert.butyl-phenyl)-3-(4'-methoxyphenyl)-propane-1,3-dione, 3-(4'-methyl)-benzylidene-bornan-2-one, methylbenzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, tocopherols (vitamin E) and ascorbic acid (vitamin C).

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone. Suitable dyes are any of the substances suitable and licensed for cosmetic purposes as listed, for example, in the publication "Kosmetische Färbemittel" of the Farbstoff-kommission der Deutschen Forschungsgemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

Various hair shampoos containing dialkyl carbonates (formulations F1 to F7) and silicone (comparison formulation F8) were evaluated for feel and shine on a scale of 1 (=pleasant soft feel, brilliant shine) to 5 (=hard, dull) by a panel of 20 volunteers in the well-known half-head test. For qualitative determination of the accumulation of the oils on the hair, hair tresses were alternately treated with the test formulations and dried 10 times and then reduced to ashes. A heavy accumulation of oils is indicated by the symbol (+) in the Table; if little or no oils could be detected, the symbol (−) is used. The results represent average values.

TABLE 1

Hair Shampoos: Feel and Shine (quantities in % by weight)

| Components | F1 | F2 | F3 | F4 | F5 | F6 | F7 | F8 |
|---|---|---|---|---|---|---|---|---|
| Sodium Laureth Sulfate | | | | 12 | | | | |
| Coco Glucosides | | | | 4 | | | | |
| Cocoamidopropyl betaine | | | | 2 | | | | |
| PEG Distearate | | | | 3 | | | | |
| Methyloctyl carbonate | 1 | — | — | — | — | — | — | — |
| Di-n-octyl carbonate | — | 1 | — | — | — | — | — | — |
| 2-Ethylhexyl lauryl + 7EO carbonate | — | — | 1 | — | — | — | — | — |
| Octyl lauryl + 7EO carbonate | — | — | — | 1 | — | — | — | — |
| Di-n-lauryl + 7EO carbonate | — | — | — | — | 1 | — | — | — |
| Di-n-cetearyl + 5EO carbonate | — | — | — | — | — | 1 | — | — |
| Tris-(2-ethylhexyl)-trimethylol carbonate | — | — | — | — | — | — | 1 | — |
| Dimethicone | — | — | — | — | — | — | — | 1 |
| NaCl | | | | 0.5 | | | | |
| Water | | | | to 100 | | | | |
| Evaluation in the half-head test | | | | | | | | |
| Feel | 2 | 2 | 2 | 1.5 | 2 | 1 | 1 | 2.5 |
| Shine | 1 | 2 | 1.5 | 2.5 | 2 | 1 | 1 | 3 |
| Accumulation | — | — | — | — | — | — | — | + |

Hair aftertreatment formulations F9 to F15 according to the invention and comparison product F16 were tested in the same way. The results are set out in Table 2.

TABLE 2

Hair Aftertreatment Formulations: Feel and Shine (quantities in % by weight)

| Components | F9 | F10 | F11 | F12 | F13 | F14 | F15 | F16 |
|---|---|---|---|---|---|---|---|---|
| Cetearyl alcohol | | | | | | | 3 | |
| Cetrimmonium chloride | | | | | | | 4 | |
| Glyceryl stearate | | | | | | | 3 | |
| Methyloctyl carbonate | 1 | — | — | — | — | — | — | — |
| Di-n-octyl carbonate | — | 1 | — | — | — | — | — | — |
| 2-Ethylhexyl lauryl + 7EO carbonate | — | — | 1 | — | — | — | — | — |
| Octyl lauryl + 7EO carbonate | — | — | — | 1 | — | — | — | — |
| Di-n-lauryl + 7EO carbonate | — | — | — | — | 1 | — | — | — |
| Di-n-cetearyl + 5EO carbonate | — | — | — | — | — | 1 | — | — |
| Tris-(2-ethyl-hexyl)-trimethylol carbonate | — | — | — | — | — | — | 1 | — |
| Dimethicone | — | — | — | — | — | — | — | 1 |
| NaCl | | | | | 0.5 | | | |
| Water | | | | | to 100 | | | |
| Evaluation in the half-head test | | | | | | | | |
| Feel | 2 | 2 | 1.5 | 1.5 | 2 | 1 | 2.5 | 3 |
| Shine | 1 | 1.5 | 1 | 2 | 2 | 1 | 2.5 | 3.5 |
| Accumulation | — | — | — | — | — | — | — | + |

The panel tests show that the fatty compounds according to the invention give formulations which are considered to perform better on the hair than silicone-containing comparison formulations and which, at the same time, have the advantage of no build-up effect.

The sensorial properties of o/w cremes containing dialkyl carbonates or silicone oils were evaluated in a so-called sensory assessment. The compositions of the formulations are set out in Table 3. Formulations 17 and 20 correspond to the invention while formulations 18, 19, 21 and 22 are intended for comparison.

TABLE 3

O/W Cremes (quantities in % by weight)

| INCL Name | F17 | F18 | F19 | F20 | F21 | F22 |
|---|---|---|---|---|---|---|
| Glyceryl stearate | 2.5 | 2.5 | 2.5 | 2.7 | 2.7 | 2.7 |
| Cetearyl alcohol | 3.8 | 3.8 | 3.8 | 4.0 | 4.0 | 4.0 |
| Capric/caprylic triglycerides | 3.6 | 3.6 | 3.6 | — | — | — |
| Petrolatum | 12.1 | 12.1 | 12.1 | — | — | — |
| Dioctyl carbonate | 5.0 | — | — | 3.3 | — | — |
| Cyclomethicone | — | 5.0 | — | — | — | — |
| Mineral oil | — | — | 5.0 | 18.7 | 18.7 | 18.7 |
| PEG-20 Glyceryl stearate | 4.4 | 4.4 | 4.4 | 4.7 | 4.7 | 4.7 |
| Dimethicone | 0.3 | 0.3 | 0.3 | — | 3.3 | — |
| Propylene glycol | 6.3 | 6.3 | 6.3 | — | — | — |
| Water | | | | to 100 | | |

Formulation 17 according to the invention is distinguished from comparison formulations 18 and 19 by faster absorption into the skin and fewer oily or wax-like residues. Formulation 20 according to the invention was found to show fewer "whitening" effects than comparison formulations 21 and 22.

What is claimed is:

1. A cosmetics or pharmaceutical formulation comprising:
(a) a dialkyl carbonate of the formula (Ia):

$$R^1O-\underset{\underset{O}{\|}}{C}-OR_2 \qquad (Ia)$$

wherein $R^1$ represents a linear alk(en)yl group having from 6 to 22 carbon atoms, and $R^2$ represents the same linear alk(en)yl group as $R^1$; and
(b) an emulsifier.

2. The formulation according to claim 1, wherein $R^1$ represents a linear alk(en)yl group having from 8 to 18 carbon atoms.

3. The formulation according to claim 1, wherein $R^1$ represents a liner alk(en)yl group having from 12 to 18 carbon atoms.

4. The formulation according to claim 1, wherein the emulsifier is selected from the group consisting of products of: the addition of 2 to 30 moles of ethylene oxide and/or 0 to 5 moles of propylene oxide to linear fatty alcohols containing 8 to 22 carbon atoms, to fatty acids containing 12 to 22 carbon atoms, and to alkylphenols containing 8 to 15 carbon atoms in the alkyl group; $C_{12-18}$ fatty acid monoesters and diesters of products of the addition of 1 to 30 moles of ethylene oxide to glycerol; glycerol monoesters and diesters and sorbitan monoesters and diesters of saturated and unsaturated fatty acids containing 6 to 22 carbon atoms and ethylene oxide adducts thereof; alkyl mono- and oligoglycosides containing 8 to 22 carbon atoms in the alkyl group and ethoxylated analogs thereof; products of the addition of 15 to 60 moles of ethylene oxide to castor oil and/or hydrogenated castor oil; polyol esters; products of the addition of 2 to 15 moles of ethylene oxide to castor oil and/or hydrogenated castor oil; partial esters based on linear, branched, unsaturated, or saturated $C_{6-22}$ fatty acids, ricinoleic acid, and 12-hydroxystearic acid and glycerol polyglycerol, pentaerythritol, dipentaerythritol, sugar alcohols, alkyl glucosides, and polyglucosides; trialkyl phosphates and mono-, di, and/or tri-PEG-alkyl phosphates; wool wax alcohols; polysiloxane/polyalkyl polyether copolymers; mixed esters of pentaerythritol, fatty acids, citric acid, and fatty alcohol and/or mixed esters of fatty acids containing 6 to 22 carbon atoms, methyl glucose, and polyols; hydrophobicized polyacrylates; polyalkylene glycols; betaines; and esterquats.

5. The formulation according to claim 1, wherein the emulsifier is selected from the group consisting of alkyl oligoglucosides, betaines, and polyglycerol poly-12-hydroxystearates.

6. The formulation according to claim 2, wherein the emulsifier is selected from the group consisting of alkyl oligoglucosides, betaines, and polyglycerol poly-12-hydroxystearates.

7. The formulation according to claim 3, wherein the emulsifier is selected form the group consisting of alkyl oligoglucosides, betaines, and polyglycerol poly-12-hydroxystearates.

8. The formulation according to claim 5, wherein (a) and (b) comprise 0.1% to 20% by weight of the formulation.

9. The formulation according to claim 6, wherein (a) and (b) comprise 0.1% to 20% by weight of the formulation.

10. The formulation according to claim 5, wherein (a) and (b) comprise 1% to 10% by weight of the formulation.

11. The formulation according to claim 6, wherein (a) and (b) comprise 1% to 10% by weight of the formulation.

12. The formulation according to claim 1, wherein (a) and (b) are present in a weight ratio of 30:1 to 1:20.

13. The formulation according to claim 5, wherein (a) and (b) are present in a weight ratio of 30:1 to 1:20.

14. The formulation according to claim 6, wherein (a) and (b) are present in a weight ratio of 30:1 to 1:20.

15. The formulation according to claim 1, wherein (a) and (b) are present in a weight ratio of 5:1 to 1:10.

16. The formulation according to claim 5, wherein (a) and (b) are present in a weight ratio of 5:1 to 1:10.

17. The formulation according to claim 6, wherein (a) and (b) are present in a weight ratio of 5:1 to 1:10.

18. The formulation according to claim 1, wherein (a) and (b) are present in a weight ratio of 1:5 to 1:10.

19. The formulation according to claim 1, wherein (a) and (b) are present in a weight ratio of 5:1 to 1:1.

20. A cosmetic or pharmaceutical formulation comprising:

(a) a dialkyl carbonated of the formula (Ia);

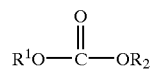

(Ia)

wherein $R^1$ represents a linear alk(en)yl group having from 12 to 18 carbon atoms, and $R^2$ represents the same linear alk(en)yl group as $R^1$; and (b) an emulsifier selected from the group consisting of alkyl oligoglucosides, betaines, and polyglycerol poly-12-hydroxystearates;

wherein (a) and (b) are present in a weight ration of 5:1 to 1:10; and wherein (a) and (b) comprise 0.1% to 20% by weight of the formulation.

* * * * *

(12) EX PARTE REEXAMINATION CERTIFICATE (5603rd)
United States Patent
Loehl et al.

(10) Number: US 6,482,418 C1
(45) Certificate Issued: Nov. 7, 2006

(54) COSMETIC AND/OR PHARMACEUTICAL PREPARATIONS COMPRISING DIALKENYL CARBONATES

(75) Inventors: Thorsten Loehl, Duesseldorf (DE); Thomas Gassenmeier, Dusseldorf (DE); Joerg Kahre, Leichlingen (DE); Hermann Hensen, Haan (DE); Holger Tesmann, Juechan (DE); Achim Ansmann, Erkrath (DE)

(73) Assignee: Henkel Kommanditgesellschaftauf Aktien (Henkel KGaA), Duesseldorf (DE)

Reexamination Request:
No. 90/006,723, Jul. 23, 2003

Reexamination Certificate for:
Patent No.: 6,482,418
Issued: Nov. 19, 2002
Appl. No.: 09/202,378
Filed: Jun. 21, 1999

(22) PCT Filed: Jun. 3, 1997

(86) PCT No.: PCT/EP97/02867
§ 371 (c)(1),
(2), (4) Date: Jun. 21, 1999

(87) PCT Pub. No.: WO97/47282
PCT Pub. Date: Dec. 18, 1997

(51) Int. Cl.
*A61K 6/00* (2006.01)

(52) U.S. Cl. .................. 424/401; 510/417; 252/50; 514/937; 514/938

(58) Field of Classification Search ............... 424/401; 514/937, 938; 510/417; 252/56
See application file for complete search history.

(56) References Cited

U.S. PATENT DOCUMENTS 5,795,978 A     8/1998    Ansmann et al. ........... 536/120

FOREIGN PATENT DOCUMENTS

DE       41 19 890 A1    12/1992
JP        H7-138586      5/1995

*Primary Examiner*—Jyothsna Venkat

(57) ABSTRACT

The invention relates to new cosmetic and/or pharmaceutical formulations containing
(a) dialkyl carbonates corresponding to formula (I):

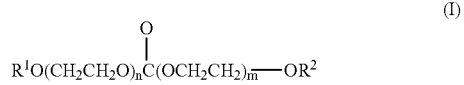

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another stand for 0 or numbers of 1 to 100, and
(b) emulsifiers.

The formulations are distinguished by particular sensorial properties, the dialkyl carbonates providing to be as effective as the silicone oils which they are intended to replace.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–20 are cancelled.

* * * * *